United States Patent [19]

Wildemeersch

[11] Patent Number: 5,433,218
[45] Date of Patent: Jul. 18, 1995

[54] INTRA-UTERINE DEVICE

[76] Inventor: Dirk Wildemeersch, Vossenhul 8, Knokke-Heist, B-8300, Belgium

[21] Appl. No.: 162,833

[22] Filed: Dec. 6, 1993

Related U.S. Application Data

[63] Continuation of Ser. No. 659,301, filed as PCT/BE89/00049, Nove. 22, 1989, abandoned.

[30] Foreign Application Priority Data

Nov. 23, 1988 [BE] Belgium .................. 08801324

[51] Int. Cl.⁶ ................................ A61F 6/06
[52] U.S. Cl. .................... 128/833; 128/832; 128/839
[58] Field of Search ............... 128/830, 832, 833, 834, 128/839-841, 835; 604/54, 55

[56] References Cited

U.S. PATENT DOCUMENTS

| | | | |
|---|---|---|---|
| 3,537,445 | 11/1970 | Burnhill | 128/839 |
| 3,598,115 | 8/1971 | Horne, Jr. | 128/833 |
| 3,757,775 | 9/1973 | Marco et al. | 128/839 |
| 3,789,838 | 2/1974 | Fournier et al. | 128/840 X |
| 3,905,360 | 9/1975 | Zaffaroni | 128/130 |
| 3,913,573 | 10/1975 | Gutnick | 128/833 |
| 3,916,898 | 11/1975 | Robinson | 604/55 |
| 3,954,103 | 5/1976 | Garcia-Roel et al. | 128/130 |
| 3,957,042 | 5/1976 | Krzakiewski et al. | 128/839 |
| 4,005,707 | 2/1977 | Moulding, Jr. | 128/839 |
| 4,117,838 | 10/1978 | Hasson | 128/833 |
| 4,377,157 | 3/1983 | Zartman | 128/830 X |
| 4,428,371 | 1/1984 | Krzeminski | 128/840 |
| 4,449,980 | 5/1984 | Millar et al. | 128/830 X |
| 4,553,536 | 11/1985 | Chiozza | 128/833 |
| 4,585,451 | 4/1986 | Millar | 128/832 X |
| 4,678,463 | 7/1987 | Millar | 128/832 X |
| 4,708,134 | 11/1987 | Wildemeersch | 128/840 |
| 4,721,105 | 1/1988 | Wildemeersch | 128/840 |
| 4,807,610 | 2/1989 | Gainutdinova et al. | 128/830 |
| 4,830,025 | 5/1989 | Gainutdinova et al. | 128/830 X |
| 4,878,905 | 11/1989 | Bloss | 604/285 X |
| 4,957,119 | 9/1990 | de Nijs | 128/833 X |
| 5,146,931 | 9/1992 | Kurz | 128/830 X |

FOREIGN PATENT DOCUMENTS

| | | | |
|---|---|---|---|
| 0100924 | 2/1984 | European Pat. Off. | |
| 0160633 | 11/1985 | European Pat. Off. | |
| 0191747 | 8/1986 | European Pat. Off. | |
| 2922051 | 12/1979 | Germany | 128/839 |
| 3234636 | 9/1983 | Germany | 128/839 |
| 1129712 | 10/1968 | United Kingdom. | |
| 1377092 | 6/1985 | U.S.S.R. | 128/839 |
| 9100714 | 1/1991 | WIPO | 128/839 |

Primary Examiner—Robert A. Hafer
Assistant Examiner—Brian E. Hanlon
Attorney, Agent, or Firm—Weingarten, Schurgin, Gagnebin & Hayes

[57] ABSTRACT

An improved intra-uterine device which is a deformable element in the form of a plastic fibre (1) releasing a substance which is active into the uterine cavity, the fibre has several strands (3, 3') or loops (2) placed side by side and held together in one assembly zone (4) of reduced dimensions in relation to the length of the said strands or loops, and of an element for attaching it in the uterine cavity, the element being in the form of filament (5) carrying a securing element (6) for hooking to the tissue of the uterus, suitable for insertion with the aid of a needle, and integral with the the fibre. The device is applicable to the field of the intra-uterine contraceptive devices and of the devices for the treatment of the uterus.

5 Claims, 1 Drawing Sheet

INTRA-UTERINE DEVICE

This application is a file wrapper continuation of application Ser. No. 07/659,301, filed as PCT/BE89/00049, Nov. 22, 1989, abandoned.

The object of the present invention is an improved intra-uterine device which is not only highly effective but is also remarkably well tolerated in the uterus.

In the field of intra-uterine devices, especially intra-uterine contraceptive devices, various solutions have been proposed to reduce the discomfort caused by the supports for the active substance and the risk of injury to the uterus. One of these solutions has been described in EP-A-0 100 924 (BAUER) which proposes an intra-uterine device consisting of an anchorage to the wall of the uterus, in the form of a screw or hook, integral with a small copper chain constituting the active substance. This chain is in the form of a single strand or a closed loop. Another solution has been proposed in BE-A-901 652, in the name of the person submitting the present application, according to which the intra-uterine contraceptive device consists of hollow elements made of a substance which is active in the uterine cavity, drilled right through and arranged end-to-end to form a longitudinal canal allowing a needle to pass, these elements being united into a non-rigid assembly, and this assembly being integral with a filament equipped with a means for hooking to the tissue of the uterus, suitable for insertion by means of a needle.

As compared with conventional intra-uterine contraceptive devices, integral with rigid platforms, the devices described in these two publications have the advantage, on the one hand, of being freely deformable and of thus following the movements of the uterus without imposing thereon restraints capable of causing pain and even injury and, on the other hand, of permitting, in conjunction with deformations of the device caused by movements of the uterus, displacement of the active elements of the latter, thus physically distributing the zone of release of the active product into the uterine cavity over a certain area.

It is the purpose of the invention to provide an intra-uterine device which will make it possible to take advantage of these movements of the uterus to increase still further the zone in which the active substance is released into the uterine cavity.

Indeed, in the devices according to the prior art, the area over which the active substance is released is limited, on the one hand, by the fact that, in a strand, or even in a single loop, any action applied to a part of the strand or loop for the purpose of causing its displacement, may have repercussions upon the other parts of the strand or loop, thus restricting their range of displacement; and, on the other hand, by the fact that the active substance is released from elements arranged consecutively in order to form a chain in the form of a strand or loop, the range of action of each link in the chain being limited by the fact that the said link is subjected to adjacent links.

The object of the present invention is an intra-uterine device of the type described in the above-mentioned two publications, i.e. consisting of a deformable element, made of a substance which is active in the uterine cavity, integral with a device for securing it to the wall of the uterus and more particularly of the type described in BE-A-901 652, in which the device for securing it to the wall of the uterus is made of a filament equipped with a means for hooking to the tissue of the uterus, suitable for insertion by means of a needle. More particularly, the object of the invention is an intra-uterine device of the above-cited type which, as compared with known intra-uterine devices, has the advantage of considerably increasing the area over which the active substance is released into the cavity in which it is located, the said increase arising from random displacement of each of the elements of the device, under the effect of movements of the uterus.

According to one characteristic of the invention, this purpose is accomplished by using, as a deformable element made of a substance which is active in the uterine cavity, a plastic fibre releasing a substance which is active into as an element for securing it to the uterine cavity, a filament carrying a means for hooking it to the tissue of the uterus, suitable for insertion with the aid of a needle, the said filament being integral with the fibre.

Fibres suitable for the implementation of the invention are, for example, polymer fibres permeable to steroids, of the type developed in recent years. These fibres release substances which are active for contraceptive or therapeutical purposes. Up to now they have been used conventionally wound round T- or 7-shaped intra-uterine platforms, like the copper filaments in contraceptive devices.

According to another characteristic of the invention, the filament carrying the means for hooking to the tissue of the uterus is rendered integral with the fibre in the assembly zone for the elements of the latter.

According to another characteristic of the invention, the fibre is coiled to form at least one loop and two strands of a length approximately equal to that of the loop, assembly of the loop and the strands being effected by means of a knot formed in the filament carrying the means for hooking to the tissue of the uterus, the said knot simultaneously assembling the various elements of the filament and securing the fibre to the filament carrying the device for hooking to the tissue of the uterus.

According to another characteristic of the invention, the fibre is formed into several strands or loops, each of which is integral with one and the same assembly element. The filament carrying the device for hooking to the tissue of the uterus is also integral with this assembly element.

According to still another characteristic of the invention, the assembly element is in the form of a ring providing an internal space large enough to permit the passage of a needle.

The invention will be better understood from the following description and from the drawing attached hereto which shows, by way of example, various embodiments of the invention, and wherein.

Figure 1:
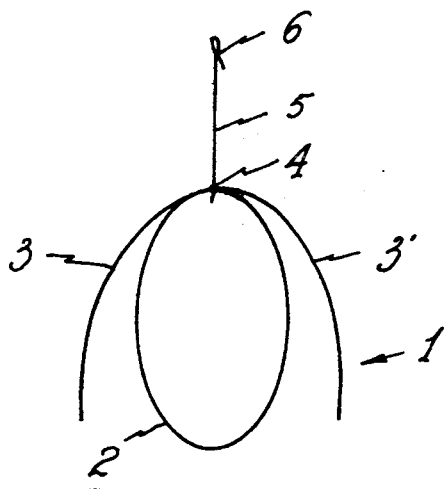
FIG. 1 is a side elevation of one embodiment of the invention.

With reference to FIG. 1, which shows an extremely simple embodiment of the invention, the intra-uterine device consists of a fibre 1 formed into a loop 2 and two strands 3, 3'. At the intersection of loop 2 and strands 3, 3', the elements of the fibre are assembled by making, around these elements, a knot 4 with the aid of a filament 5, the other end of which also comprises a knot 6 constituting a device for hooking to the tissue of the uterus, suitable for insertion with the aid of a needle. Knot 4 thus establishes an assembly zone of reduced dimensions.

Figure 2:
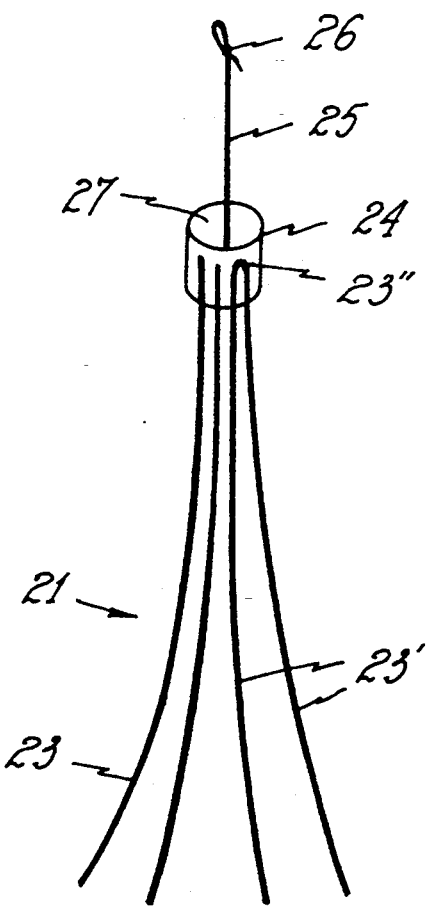
FIG. 2 is a perspective view of another embodiment of the invention.

According to FIG. 2, fibre 21 is in the form of strands 23, 23' integral with an assembly element 24 in the form of a ring. Also secured to this assembly element is a filament 25 the other end of which is shaped in 26 to provide a device for hooking to the tissue of the uterus. Space 27 inside ring 24 is large enough to allow the passage of a needle insuring insertion of the device 26 for hooking into the tissue of the uterus. Strands integral with assembly element 24 may be either simple strands like strand 23 or strands 23' folded centrally at 23" and rendered integral with assembly element 24. Here again, assembly element 24 defines an assembly zone of reduced dimensions.

Figure 3:
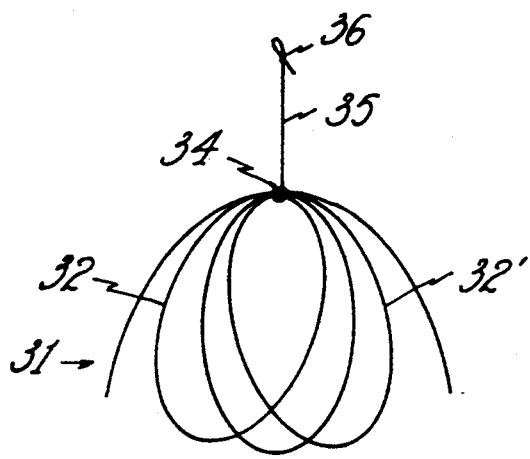
FIG. 3 is a side elevation of still another embodiment of the invention.

With reference to the embodiment illustrated in FIG. 3, fibre 31 is formed into loops 32, 32' held together by an assembly element 34, for example a spot of glue, filament 35 being also held in this assembly element and carrying at its other end a knot 36 constituting an element for hooking to the tissue of the uterus, suitable for insertion with the aid of a needle.

Figure 4:
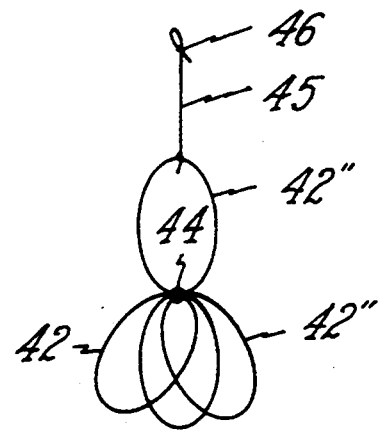
FIG. 4 is a side elevation of still another embodiment of the invention, similar to that in FIG. 3 except as regards the location where the filament carrying a device for hooking to the tissue of the uterus is rendered integral with the fibre.

Finally, the embodiment illustrated in FIG. 4 is almost identical with that in FIG. 3. Fibre 41 is in loops 42, 42' held together by an assembly element 44. It differs from the embodiment according to FIG. 3 in that filament 45, terminating in a knot 46 constituting the device for hooking to the tissue of the uterus, is secured to a loop 42" of the fibre and not to assembly element 44.

In these last two embodiments, the assembly element also defines an assembly zone of reduced dimensions.

According to the various embodiments described hereinbefore, because they are assembled one to the other in a single zone of reduced dimensions, the various elements of the fibre are free, outside this zone, to move individually in the uterus under the influence of the movements thereof, thus ensuring improved distribution, in the uterus, of the active substance released by the fibre. Obviously a given uterine device may combine different fibres releasing different active substances.

The advantage of an intra-uterine device according to the invention is that it is adapted to cover a relatively large area in relation to the dimension of the fibres, such as for instance the whole of the cavity of the uterus, and that it can easily be arranged in a definitely narrower space such as the cervix of the uterus, whereas its securing device makes it possible to select at will the best location for the desired treatment. Thus the securing device may be located either in the wall at the bottom of the uterus, in which case the fibre acts in the uterine cavity, or at the end of the cervix, at the inlet to the uterus, in which case the fibre acts in the uterine canal.

The variety of hormones capable of being released by the polymer fibres, namely estradiol and progesterones, make the device according to the invention a particularly effective instrument for different applications. The device is first of all effective as a contraceptive comprising fibres releasing progestogens, releasing these progestogens so that they are distributed perfectly either in the uterine cavity or in the uterine canal where they bring about a transformation of the cervical mucus, rendering it impermeable to spermatozoids, these various modes of action resulting form the choice of the location of the device for hooking to the tissue of the uterus. The device according to the invention also constitutes an instrument which is highly effective in the treatment of menorrhagia, and in the treatment of menopause problems, compensating by the topical release of progesterone the effects which could be disastrous for the uterus of a systemic replacement treatment with oestrogen. Furthermore, in this latter case, the most uniform possible distribution of the progesterone released in the uterine cavity is of importance in suitable local application.

I claim:

1. An intra-uterine device consisting essentially of:
   a deformable element comprising a plurality of plastic fibers, said plastic fibers being freely movable relative to each other, free to contact each other, and able to freely deform individually and spread into a pattern that is not preformed by said element, all of said plastic fibers being free to simultaneously spread into an unpreformed pattern while at rest in a uterine cavity, wherein a plastic fiber of said plurality of plastic fibers is releasably permeated with a substance which is active in a uterine cavity;
   means for holding said plurality of fibers together in an assembly zone, said holding means being of a dimension which is smaller than the length of each of said fibers; and
   means for securing the device to a uterine wall, said securing means comprising a filament integral with means cooperative with an insertion needle for hooking the device to the uterine wall.

2. The device of claim 1, wherein said filament of said securing means is integrally formed with said holding means in said assembly zone.

3. The device of claim 1 or 2, wherein:
   said plurality of plastic fibers forming at least one loop and two strands, the length of said strands together being approximately equal to the length of said loop, and
   said holding means consisting essentially of a knot formed in said filament of said securing means, whereby said knot assembles said loop and strands together in a coil and secures said fibers to said filament.

4. The device of claim 1 or 2, wherein the holding means consisting essentially of a ring having an opening therein sized to allow passage of an insertion needle.

5. The device of claim 1, wherein the holding means consisting essentially of a spot of glue.

* * * * *